United States Patent [19]

Druding et al.

[11] Patent Number: 5,133,374
[45] Date of Patent: Jul. 28, 1992

[54] APPARATUS AND METHOD FOR PURGING MEDICAL INSTRUMENTS AND DISPOSING OF INFECTIOUS WASTE

[76] Inventors: Kevin W. Druding, 2055 E. Decatur, Mesa, Ariz. 85203; William L. Merkle, 5228 E. Carolina, Scottsdale, Ariz. 85254

[21] Appl. No.: 678,800

[22] Filed: Apr. 1, 1991

[51] Int. Cl.⁵ ............................ B08B 3/04; B08B 9/08
[52] U.S. Cl. .................... 134/104.2; 15/353; 134/169 R
[58] Field of Search .................. 15/304, 321, 353; 134/104.2, 169 R, 169 C

[56] References Cited

U.S. PATENT DOCUMENTS

| 2,915,073 | 12/1959 | Merritt | 134/169 C X |
|---|---|---|---|
| 2,993,494 | 7/1961 | Svensson | 134/169 C |
| 3,040,755 | 6/1962 | Sigmon et al. | 134/169 C |
| 3,818,537 | 6/1974 | Evans | 15/321 |
| 3,874,022 | 4/1975 | Wogoman et al. | 15/321 |
| 3,963,438 | 6/1976 | Banez | 21/58 |
| 4,299,244 | 11/1981 | Hirai | 134/102 |
| 4,485,830 | 12/1984 | Icking et al. | 134/100 |
| 4,526,622 | 7/1985 | Takamura et al. | 134/21 |
| 4,579,597 | 4/1986 | Sasa et al. | 134/21 |
| 4,667,691 | 5/1987 | Sasa | 134/169 C |
| 4,819,677 | 4/1989 | Stern | 134/104.2 |
| 4,821,367 | 4/1989 | McAllister et al. | 15/353 |
| 4,826,539 | 5/1989 | Harpold | 134/10 |
| 5,022,114 | 6/1991 | Kauffeldt et al. | 15/321 X |

FOREIGN PATENT DOCUMENTS

| 180039 | 12/1935 | Switzerland | 15/353 |
|---|---|---|---|
| 1045376 | 10/1966 | United Kingdom | 134/169 R |

*Primary Examiner*—Philip R. Coe
*Attorney, Agent, or Firm*—Warren F. B. Lindsley

[57] ABSTRACT

An apparatus for transmitting infections medical waste to a sewer without personnel exposure employing a closed container having a waste tube and a suction tube extending thereinto. The waste is transmitted from an endoscope or other source into the container and the container is drained to a sewer under control of a vacuum applied to the inside of the container. The automated container drainage affords virtually unlimited container volume for improved cleaning of instrument internal channels.

9 Claims, 2 Drawing Sheets

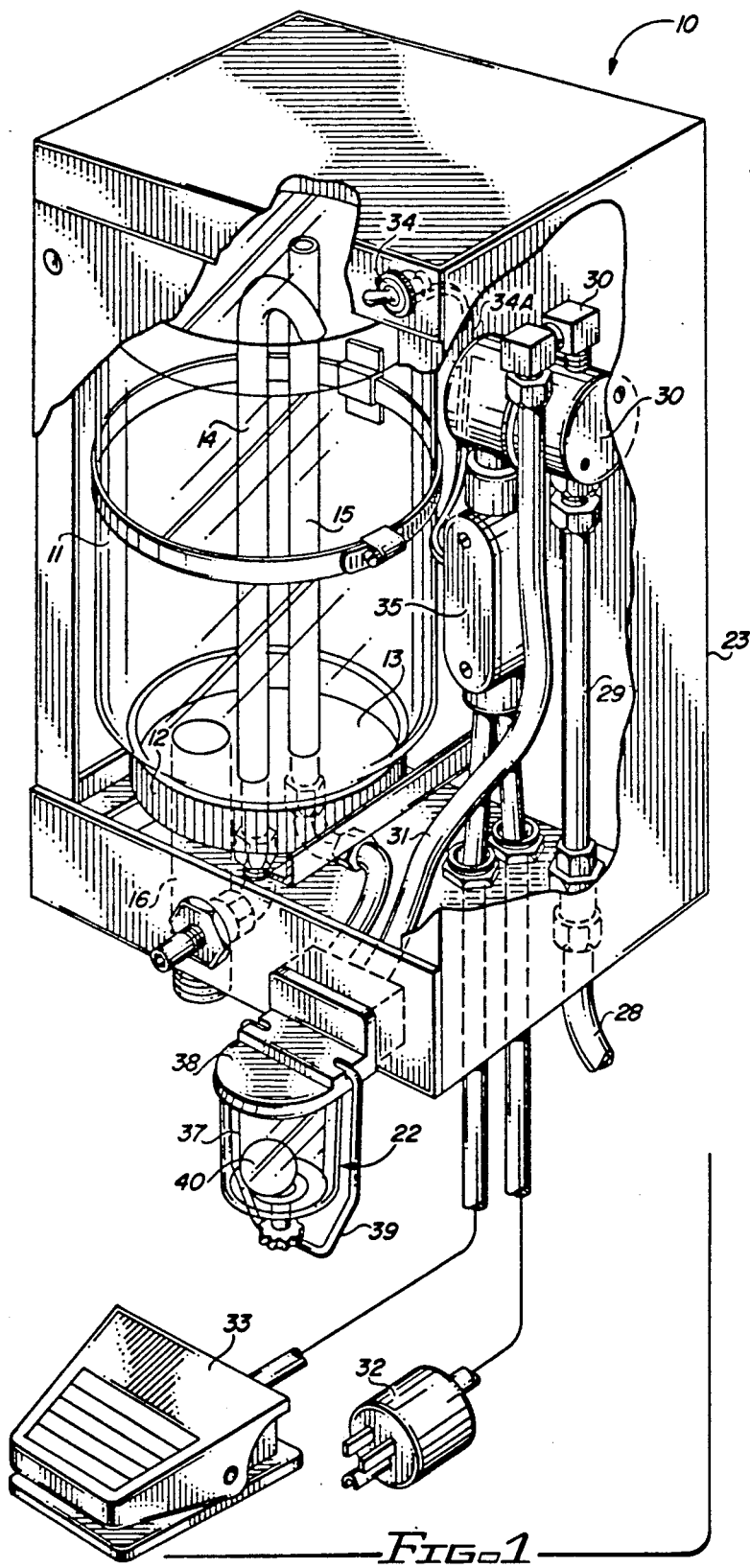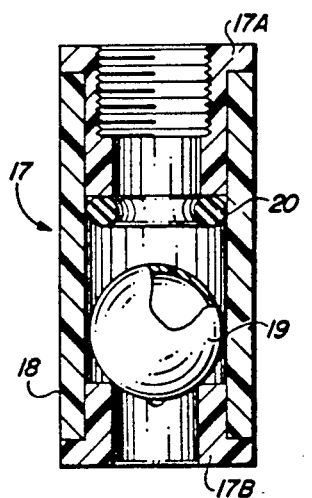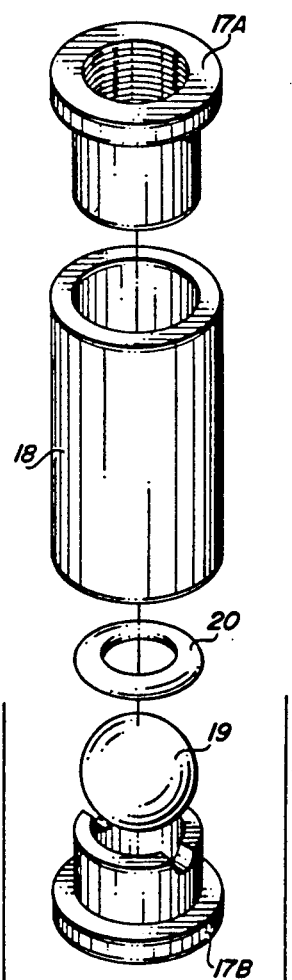
FIG. 1
FIG. 3
FIG. 4

APPARATUS AND METHOD FOR PURGING MEDICAL INSTRUMENTS AND DISPOSING OF INFECTIOUS WASTE

BACKGROUND OF THE INVENTION

The present invention relates to the disposal of infectious medical wastes and more particularly to the disposal of secretions and excretions from internal channels of medical instruments.

In medical practice, it is common to insert medical instruments into an organ of a patient, after which these instruments must be purged, disinfected and sterilized before further use. Secretions and excretions which pass through such instruments during procedure must also be disposed of, and this invention provides for such disposal without personnel exposure.

Two methods are currently employed for disposal of such infectious medical waste: In the first method, the waste is collected in a reusable container during procedure. Following a procedure, the container is emptied into an open hopper, thereby presenting a high risk to the personnel handling the container of exposure to infectious matter due to splashing or spilling of the waste as it is discarded. The present invention automates the disposal of waste from the container following a procedure.

The second method for disposal of infectious medical waste involves the use of disposable containers, typically plastic, which replace the reusable container referred to in the first method described above. The disposable containers provide modest protection to personnel since it is not common practice to empty these disposable containers into open hoppers; however, the risk of exposure is still present during required sealing, handling and transporting of the filled disposable containers to a disposal site. In addition, the disposable containers present a detrimental environmental impact upon their disposal. The non-biodegradable plastic releases toxic chlorine gas upon incineration, or otherwise detrimentally impacts the environment in a landfill. The present invention eliminates the requirement for the disposable containers, thereby eliminating associated risk of personnel exposure to infectious matter as well as eliminating detrimental environmental impact.

In addition to minimizing risk of personnel exposure to infectious matter, the present invention affords an improvement to existing methods of cleaning and drying the internal channels of an endoscope. This is accomplished by substantially continuous suction flow thorough the instrument channels thereby drying the channels more rapidly than possible with existing devices. The present invention also provides virtually unlimited capacity for solutions drawn through instrument channels where existing container size limits volume of solution which is employed during cleaning. In addition, the present invention significantly reduces time required for instrument rinsing by employing suction for this operation in place of manually operating a syringe.

DESCRIPTION OF THE PRIOR ART

Management of hazardous materials and waste has become a major concern of hospitals in recent years, due to the intensified regulation, litigation and high costs associated with this aspect of health care. An additional concern relates to cleaning and disinfection of devices which potentially come into contact with the personnel. This concern resulted in the granting of the following patents, which although of interest, are not anticipatory of the invention claimed herein.

U.S. Pat. No. 2,993,494 is directed to an apparatus for cleaning milking machines having through flow channels.

U.S. Pat. No. 3,040,755 is directed to an apparatus for washing parts of a pipe line milking system coming in contact with milk without requiring dismantling of the milking system.

U.S. Pat. No. 3,963,438 discloses a method of sterilizing a fiberoptic proctoscope.

U.S. Pat. No. 4,299,244 discloses an endoscope washing apparatus in which the optical fiber tube of an endoscope is submerged in flowing water into which a multiplicity of air streams are injected to produce a myriad of foams.

U.S. Pat. No. 4,485,830 discloses a cleansing arrangement for a milking machine which conveys both acidic and alkaline cleansing fluids into the metering device with little danger of the formation of crystalline deposits in the region where the cleansing fluids enter the metering device.

U.S. Pat. No. 4,526,622 discloses a method of cleaning the channels of an endoscope, one end of a suction device and a nozzle, both positioned at the distal end of an insertion section of the endoscope.

U.S. Pat. No. 4,579,597 discloses a method of cleaning the channels and valve cylinders of an endoscope.

U.S. Pat. No. 4,667,691 discloses a device for cleaning channels of an endoscope employing a check valve for permitting suction of a liquid detergent into the device and employing a syringe for effecting suction and discharge of the liquid detergent.

U.S. Pat. No. 4,819,677 discloses a container for hazardous detergents.

U.S. Pat. No. 4,826,539 discloses an apparatus and method for cleaning printing screens in which solvent is pumped from a reservoir to the surface to be cleaned.

SUMMARY OF THE INVENTION

This invention relates to a method and apparatus for collection and disposal of medical infectious liquid waste. The apparatus incorporates a container into which two transfer tubes protrude, and which features a drain valve which is closed during accumulation (collection), and open during disposal. The apparatus utilizes suction to draw air from the container via one of the transfer tubes, thereby creating a vacuum in the container. The resultant vacuum in the container draws matter into the container via the second transfer tube, which is connected to the medical instrument. This invention automates the action of emptying the container prior to future use and also automates container cleaning during an instrument cleaning function.

It is, therefore, one object of this invention to provide new and improved apparatus for disposing of medical liquid waste, particularly from an endoscope, without personnel exposure.

Another object of this invention is to provide a suction device which discharges secretions and excretions to a drain without personnel exposure.

A further object of this invention is to provide an endoscope cleaning process in combination with an improved apparatus and method for discharging infectious medical waste handled by the endoscope without personnel expsoure.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 1 is a perspective view of a device for cleaning and disposing of the secretions and excretions from an endoscope;

FIG. 3 is a cross sectional view of the ball valve assembly shown in FIG. 2;

FIG. 4 is an exploded view of the ball valve assembly shown in FIG. 3;

DESCRIPTION OF THE PREFERRED EMBODIMENT

Figure 2:
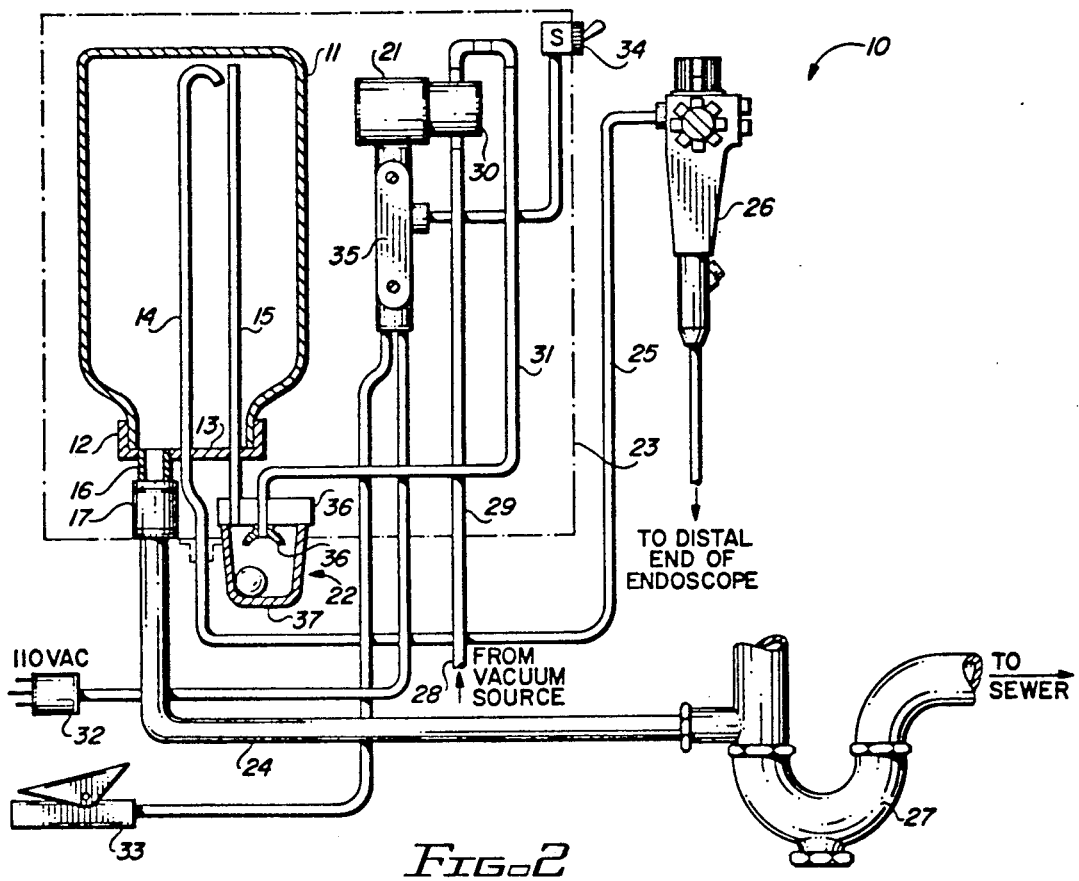
FIG. 2 is a diagrammatic illustration of the device shown in FIG. 1 connected to a disposal system.

Referring more particulalry to the drawings by characters of reference, FIGS. 1 and 2 disclose an apparatus employing suction to accumulate medical waste and, by interrupting the suction, causing drainage to a waste or disposal site. In the preferred embodiment, a sealed container is fitted with two transfer tubes and a drain port for the waste collection and disposal functions. One of the transfer tubes serves to evacuate the container when suction is applied and the other is used to transfer waste into the container under vacuum conditions. A valve at the container drain is closed to seal the container during suction; otherwise the drain valve is open to permit drainage and venting.

Both the suction and waste inlet transfer tubes enter the container bottom and project upwardly to a point just below the top of the container. The waste inlet tube is bent in a 160° arc to direct inlet flow downwardly impinging on the walls inside of the container. This impingement effects container cleaning when solvents or sterilants are drawn through the apparatus. The suction transfer tube terminates at a point in the container which is at a higher elevation than the waste inlet transfer tube to afford maximum container capacity without overflow or ingestion of the waste into the suction circuit. A shut-off valve in the suction circuit provides positive interruption of suction in the event of overflow. A normally closed solenoid upstream of the overflow shut-off valve interrupts suction flow as demanded by the operation of electrical switches controlling electrical power to the solenoid.

FIGS. 1 and 2 disclose an apparatus 10 for purging medical instruments and disposing of the infectious waste therefrom which comprises a reusable reservoir or container 11 and its cover 12, a plate assembly 13 consisting of a waste inlet transfer tube 14, a suction transfer tube 15 and a fitting 16 for connecting a ball valve assembly 17 to assembly plate 13.

Ball valve assembly 17 comprises a housing 18 having top and bottom seats 17A and 17B respectively in which a ball 19 and ball seat 20 are provided which assembly serves to seal the container when suction flow is commanded through the apparatus.

This ball valve is a single-seat check valve which closes by drawing ball 19 into its seat 20 when suction is applied to apparatus 10 as later explained. Upon initiation of suction, container 11 is sealed by ball valve assembly 17 at fitting 16. Ball 19 will be forced away from its seat 20 when the pressure at ball seat 20 is equal to or greater than pressure in drain line 24. The internal geometry of housing 18 permits fluid flow around ball 19 when it is unseated.

Apparatus 10 further comprises a three port normally closed electro-pneumatic solenoid 21 which, for example, may comprise a Schrader-Bellows Corporation product, and an overflow shut off valve assembly 22 which may, for example, comprise an Everest and Jennings, Inc. product.

Selection of interconnecting tubing and associated fittings has been made to assure unrestricted flow of air and fluid within the range of flow rates experienced during service. Component placement within housing 23, shown in FIG. 1, assures user access to the overflow shutoff valve 22 and provide positive protection for electrical components by placing them above the highest operational fluid levels in housing 23.

Container cover 12 is specially fabricated to seal plate assembly 13 in container 11 in a manner similar to a mason or canning jar top. Cover 12 is designed for a 110 millimeter opening of the container since such a part does not exist commercially for openings larger than 86 millimeters.

The plate assembly 13 includes the two transfer tubes 14 and 15 together with fitting 16, all welded to plate 13. The waste inlet transfer tube 14 is curved to effect fluid impingement on the wall of container 11 with suction transfer tube 15 projecting upwardly in container 11 to a higher point than waste transfer tube 14 in order to afford maximum container capacity without overflow. Both tubes 14 and 15 protrude outwardly of container 11 through plate 13. Fitting 16 is a common pipe threaded nipple which provides attachment means for ball valve assembly 17. The inside surface of plate 13 is smooth to minimize adhesion of waste thereto.

The plumbing system for apparatus 10 comprises a fluid or waste portion for directing waste into container 11 via pipe line 25 from endoscope 26 causing container 11 to fill. Container 11 is sealed by plate 13 and cover 12 with waste being discharged from container 11 via fitting 16, pipe line 24 and trap 27 to a sanitary sewer.

The suction portion of the plumbing is connected to a suitable vacuum source such as an aspirator pump or to a suction system available in most institutional facilities. The purpose of the suction circuit is to maintain a vacuum in container 11 so as to draw waste into and from endoscope 26 through pipe line 25, waste transfer tube 14 and into container 11. Air under suction flows from a source 28 through pipe line 29, solenoid controls 30, flexible pipe line 31, overflow valve 22, and suction transfer tube 15 thus completing the suction circuit from the vacuum source to container 11.

Solenoid control 21 is the only system component requiring electrical power. Electrical power is applied to solenoid control 21 from a suitable source such as 110 voltage alternating current source through a plug 32. A footswitch 33 may supply and interrupt the electrical power when an intermittent vacuum source is required. Where continuous suction is required, a toggle switch 34 is provided for controlling solenoid control 21 through wire 34A. A junction box 35 is provided in which switching under control of footswitch 33 and toggle switch 34 is provided in a known manner.

The three-port feature of solenoid 30 provides complete drainage of container 11. In the closed (power off) position, solenoid control 21 interrupts suction flow through solenoid 30 while permitting ambient air flow within housing 23 to flow through solenoid 30, pipe line 31, shut off valve 22 and into container 11 through suction transfer tube 15. This provides for venting of container 11 and accelerates drainage of container 11. In the open(power on) position, solenoid control 21 connects vacuum source 28 to suction inlet flow tube 15 while interrupting ambient airflow into container 11.

As noted from FIGS. 1 and 2 of the drawings, flexible tubing or pipe line 31 and suction transfer tube 15 are connected to the overflow cut off valve 22. Suction transfer tube 15 provides a means for the contents of container 11 to flow into a valve trap 37 of valve 22 which is clamped and sealed to a valve cap 38 by a bail clamp 39 and suitable gasket (not shown). A buoyant ball 40 is normally at the bottom of trap 37 permitting unobstructed flow between suction transfer tube 15 and flexible tubing or pipe line 31 via an internal air passage in valve 22. The internal air passage connects a ball seat 36 in valve 22 to pipe line 31. In the event of waste overflow, the buoyant ball 40 is forced into this ball seat as a result of floating on the surface of overflowing fluid thereby preventing fluid flow into pipe line 31. The overflow valve 22 protects solenoid 21 and the suction source from contamination in the event of waste overflow in container 11.

Housing 23 is preferably a stainless steel enclosure the interior of which is adapted with bracketry to mount overflow valve 22 and to support container 11. Through holes are strategically located in housing 23 for mounting solenoid 21, toggle switch 34, waste inlet 14, drain fitting 16 and for routing of electrical wires for plug 32 and footswitch 33. Keyhole shaped mounting holes (not shown) on the back of housing 23 provide for convenient wall mounting.

Figures 5, 6:
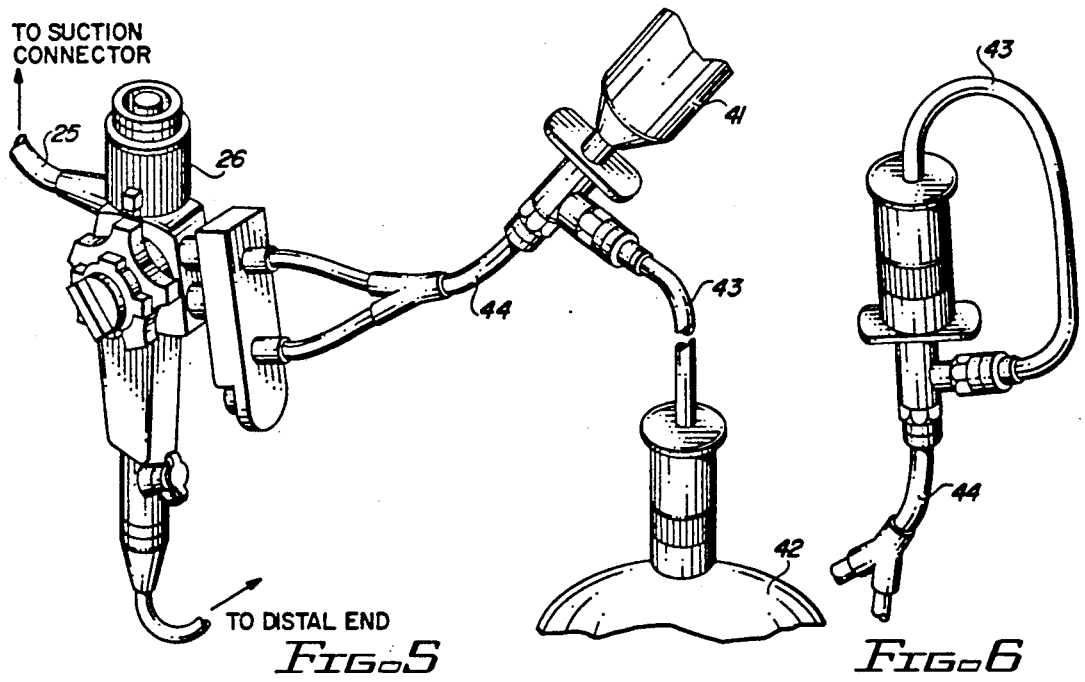
FIG. 5 is a partial perspective view of the endoscope shown in FIG. 2 and illustrates the sterilant connected to the valving arrangment, i.e., irrigator, for sterilizing the endoscope.
FIG. 6 is a method of dead ending the sterilant connection shown in FIG. 5 for simultaneous irrigation of the endoscope's internal channels.

FIG. 5 illustrates a means of adding or discharging the contents of a syringe 41 into the suction system of endoscope 26 while drawing a cleaning solution or gas from a container 42 through pipe line 43 and 44 into suction connector 25 for cleaning the internal passageways of the endoscope.

FIG. 6 illustrates a way of dead ending the connection to the endoscope shown in FIG. 5. This is conducted when the cleaning fuction of apparatus 10 is completed and the endoscope is submerged in the sterilant. In addition, the dead ended connection permits simultaneous rinsing of all instrument internal channels.

Although but one embodiment of the invention has been illustrates and described, it will be apparent to those skilled in the art that various changes and modifications may be made therein without departing from the spirit of the invention or from the scope of the appended claims.

What is claimed is:

1. An apparatus for transmitting infectious medical waste to a sewer without personnel exposure comprising:
   a closed container,
   said container having a waste inlet tube and a suction tube extending thereinto,
   a drainage tube for draining waste from said container,
   a first means for connecting said waste inlet tube to a source of infectious medical waste,
   a second means for connecting said suction tube to a vacuum source,
   said second means comprising an overflow valve for controlling the connection of said vacuum source to said suction tube dependent upon the amount of waste in said container,
   a valve assembly for draining said container to a sewer when containing said waste and sealing said container from the sewer when it is subjected to a vacuum from said suction tube, and
   a third means for selectively connecting said vacuum source to said suction tube.

2. The apparatus set forth in claim 1 wherein:
   said third means comprises a solenoid means.

3. The apparatus set forth in claim 1 wherein:
   said valve assembly comprises a ball valve mounted in said drainage tube.

4. The apparatus set forth in claim 3 wherein:
   said source of infectious waste comprises an endoscope.

5. The apparatus set forth in claim 4 in further combination with:
   a source of cleaning solution for drawing into said endoscope for cleaning the internal channels of the endoscope and said suction tube.

6. The apparatus set froth in claim 1 in further combination with:
   a source of infectious medical waste.

7. The apparatus set forth in claim 1 wherein:
   said third means comprises a switching means for selectively energizing a solenoid for connecting and disconnecting said vacuum source to said suction tube.

8. The apparatus set forth in claim 1 wherein:
   said third means connects said suction tube to atmosphere for aiding in draining said container through said drainage tube.

9. The apparatus set forth in claim 1 wherein:
   said overflow valve comprises a housing to which said suction tube and said vacuum source are connected, a valve seat and a ball for seating in said valve seat when waste enters said housing.

* * * * *